United States Patent
McNally et al.

[11] Patent Number: 6,142,979
[45] Date of Patent: Nov. 7, 2000

[54] PINCH CLIP OCCLUDER SYSTEM FOR INFUSION SETS

[75] Inventors: David J. McNally, Bluffdale; Al Halbert, Salt Lake City, both of Utah

[73] Assignee: Zevex, Salt Lake City, Utah

[21] Appl. No.: 09/158,590

[22] Filed: Sep. 22, 1998

Related U.S. Application Data

[63] Continuation-in-part of application No. 08/712,577, Sep. 13, 1996, Pat. No. 5,810,323, which is a continuation of application No. 08/410,912, Mar. 21, 1998, abandoned.

[51] Int. Cl.[7] ..................................................... A61M 5/00
[52] U.S. Cl. ........................ 604/246; 604/500; 248/68.1
[58] Field of Search ................. 211/87.01, 60.1; 248/68.1; 604/250, 251, 246, 500

[56] References Cited

U.S. PATENT DOCUMENTS

| | | |
|---|---|---|
| 2,471,623 | 5/1949 | Hubbell . |
| 2,858,095 | 10/1958 | Harris et al. . |
| 3,213,882 | 10/1965 | Beatty . |
| 3,329,391 | 7/1967 | Deane . |
| 3,998,364 | 12/1976 | Hollander . |
| 4,230,151 | 10/1980 | Jonsson . |
| 4,236,880 | 12/1980 | Archibald . |
| 4,382,453 | 5/1983 | Bunjan et al. . |
| 4,425,116 | 1/1984 | Bilstad et al. . |
| 4,453,295 | 6/1984 | Laszczower . |
| 4,524,802 | 6/1985 | Lawrence et al. . |
| 4,559,045 | 12/1985 | Danby et al. . |
| 4,624,663 | 11/1986 | Danby et al. . |
| 4,634,092 | 1/1987 | Daniell et al. . |
| 4,645,489 | 2/1987 | Krumme et al. . |
| 4,689,043 | 8/1987 | Bisha . |
| 4,728,324 | 3/1988 | Steigerwald et al. . |
| 4,960,259 | 10/1990 | Sunnanvader et al. . |
| 5,083,561 | 1/1992 | Russo . |
| 5,219,327 | 6/1993 | Okada . |
| 5,238,218 | 8/1993 | Mackel . |
| 5,257,978 | 11/1993 | Haber et al. . |
| 5,704,584 | 1/1998 | Winterer et al. . |
| 5,810,323 | 9/1998 | Winterer et al. . |

FOREIGN PATENT DOCUMENTS

| | | |
|---|---|---|
| 0150666A1 | 9/1984 | European Pat. Off. . |
| 0423978A2 | 10/1990 | European Pat. Off. . |
| 0483794A1 | 10/1991 | European Pat. Off. . |

*Primary Examiner*—Glenn K. Dawson
*Assistant Examiner*—Jeremy Thissell
*Attorney, Agent, or Firm*—Morriss, Bateman, O'Bryant & Compagni, P.C.

[57] ABSTRACT

A pinch clip occluder system for infusion sets includes a housing and a clamp movably disposed within the housing to selectively occlude an infusion set. The pinch clip nests in an adapter placed on an enteral feeding pump such that when the pinch clip occluder is properly position, flow is allowed through the infusion set, but when the pinch clip occluder is not properly positioned in the adapter, flow through the infusion set is prevented.

26 Claims, 11 Drawing Sheets

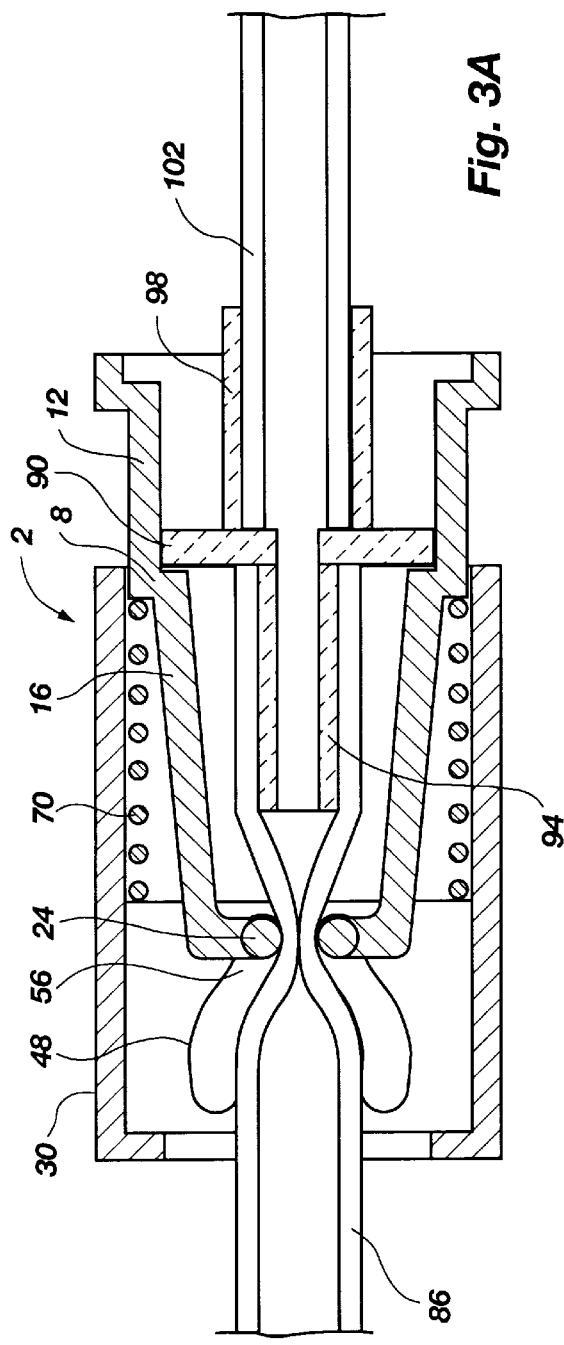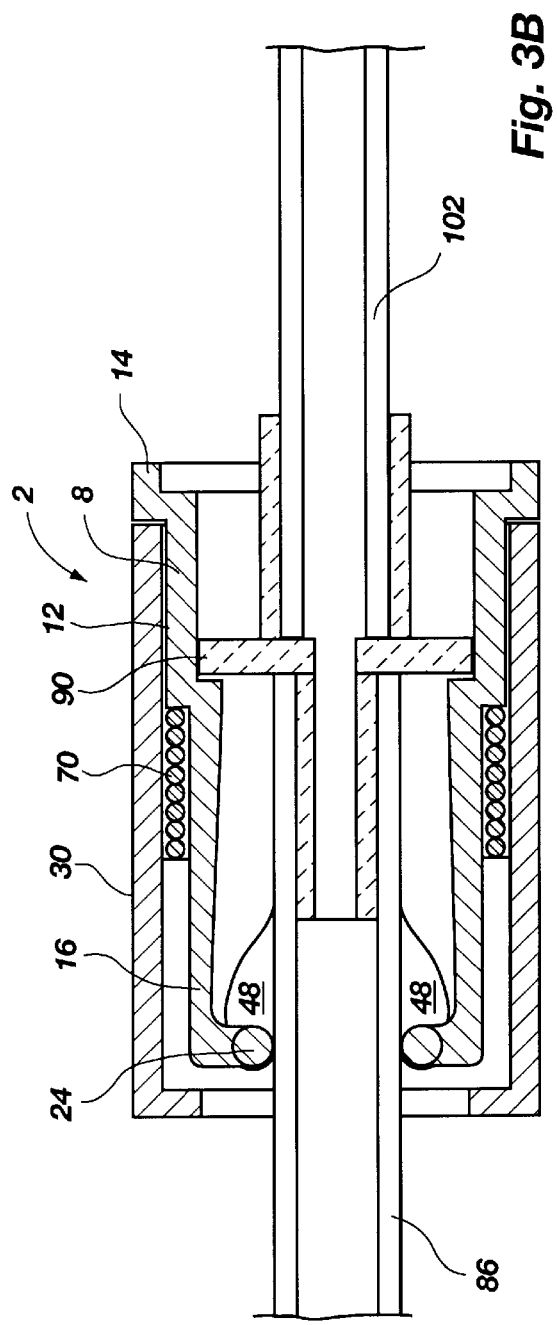

PINCH CLIP OCCLUDER SYSTEM FOR INFUSION SETS

RELATED APPLICATIONS

The present application is a continuation-in-part of U.S. patent application Ser. No. 08/712,577 filed Sep. 13, 1996, now U.S. Pat. No. 5,810,323 which is a continuation of U.S. patent application Ser. No. 08/410,912 filed Mar. 21, 1998, now abandoned.

BACKGROUND OF THE INVENTION

1. Field of the Invention

The present invention relates to an occluder system for the administration of enteral and/or parenteral solutions. More particularly, the present invention relates to a pinch clip occluder for use on infusion sets and the like, wherein the pinch clip occluder prevents the free-flow-flow of solution through the infusion set unless the pinch clip occluder is properly mounted in a housing or some other structure. Additionally, the present invention relates to an adapter which may be retrofit onto existing enteral feeding pumps and the like to enable the use of a pinch clip occluder to prevent free-flow conditions.

2. State of the Art

The use of infusion sets to administer solutions to patients is well known in the medical arts. Infusion sets are used for both enteral and parenteral applications. Enteral feeding pumps are used to provide patients with nutrition and medication when they are unable, for a variety of reasons, to eat normally. Parenteral (intravenous) solutions are provided to patients to ensure adequate hydration and to provide needed nutrients, minerals and medication. Often, the infusion set is placed in a free standing arrangement in which gravity forces the solution into the patient. The rate at which the solution enters the patient can be roughly controlled by various clamps, such as roller clamps, which are currently available on the market.

In many applications, it is necessary to precisely control the amount of solution which enters the patient. When this is the case, a regulating device, such as an enteral feeding pump, is placed along the infusion set to control the rate at which the solution is fed to the patient. In applications where a pump, etc., is used, the clamps used to regulate flow are typically opened to their fullest extent to prevent the clamp from interfering with the proper functioning of the pump. The clamp is opened with the expectation that the enteral feeding pump will control fluid flow through the infusion set. However, emergencies or other distractions may prevent the medical personnel from properly loading the infusion set in the enteral feeding pump. Furthermore, the infusion set may be inadvertently dislodged from the pump during operation of the pump.

When the infusion set is not properly loaded in the pump and the clamp has been opened, a situation known as free-flow often develops. The force of gravity causes the solution to flow freely into the patient unchecked by the pump or other regulating device. Under a free-flow condition, an amount of solution many times the desired dose can be supplied to the patient within a relatively short time period. This can be particularly dangerous if the solution contains potent medicines or the patient's body is not physically strong enough to adjust to the large inflow of solution.

Thus, there is a need for a device that prevents a free-flow condition if the infusion set is not properly mounted in the pump or other regulating means.

SUMMARY OF THE INVENTION

It is an object of the present invention to provide a safety occluder for infusion sets which prevents an accidental free-flow condition.

It is another object of the present invention to provide an occluder which is simple to make and use.

It is another object of the present invention to provide such an occluder which is inexpensive and thus disposable.

It is still another object of the present invention to provide an adapter for use on an enteral feeding pump or other device using an infusion set which enables use of a pinch clip occluder to occlude fluid flow through the infusion set unless the infusion set is properly loaded.

It is still yet another object of the present invention to provide such an adapter which may be retrofitted on existing pumps to improve safety and prevent free-flow conditions.

The above and other objects of the invention are realized in a pinch clip occluder biased in an occluding position to prevent free-flow conditions. In one embodiment of a pinch clip occluder, the occluder includes a housing with a passage therethrough and a pinch clamp nestable in the housing. The pinch clamp includes arms which are typically biased in a closed position when no external force is acting thereon, but which may be moved into an open/nonoccluding position by movement of the clamp relative to the housing.

In another illustrated embodiment, the occluder includes a housing with a passage therethrough for receiving a delivery set. A plunger disposed along the housing is movable between two positions, one of which occludes flow through the delivery set and the other of which allows flow through the delivery set. To overcome the risk of a free-flow condition, the plunger is typically biased in an occluding position.

In accordance with one aspect of the invention, a biasing member, such as a spring, is disposed between the housing and part of the plunger or pinch clamp to bias the plunger or pinch clamp in a closed position until the infusion set is properly mounted in a flow regulating device, such as an enteral feeding pump.

In accordance with another aspect of the invention, the pump housing is configured to selectively receive the pinch clip occluder. When the infusion set is properly mounted on the enteral feeding pump, etc., the pinch clip occluder is placed in such a position that fluid flow is allowed through the infusion set. If the infusion set is not properly loaded or is removed or dislodged from the pump, the pinch clip occluder will terminate fluid flow through the infusion set and thereby prevent the free-flow of solution to the patient.

BRIEF DESCRIPTION OF THE DRAWINGS

The above and other objects, features and advantages of the invention will become apparent from a consideration of the following detailed description presented in connection with the accompanying drawings in which:

FIG. 3A shows a side cross-sectional view of a pinch clip occluder made in accordance with the principles of the present invention, and disposed in an occluding mode;

FIG. 3B shows a side cross-sectional view of a pinch clip occluder made in accordance with the principles of the present invention, and disposed in a nonoccluding mode;

DETAILED DESCRIPTION

Figure 1:
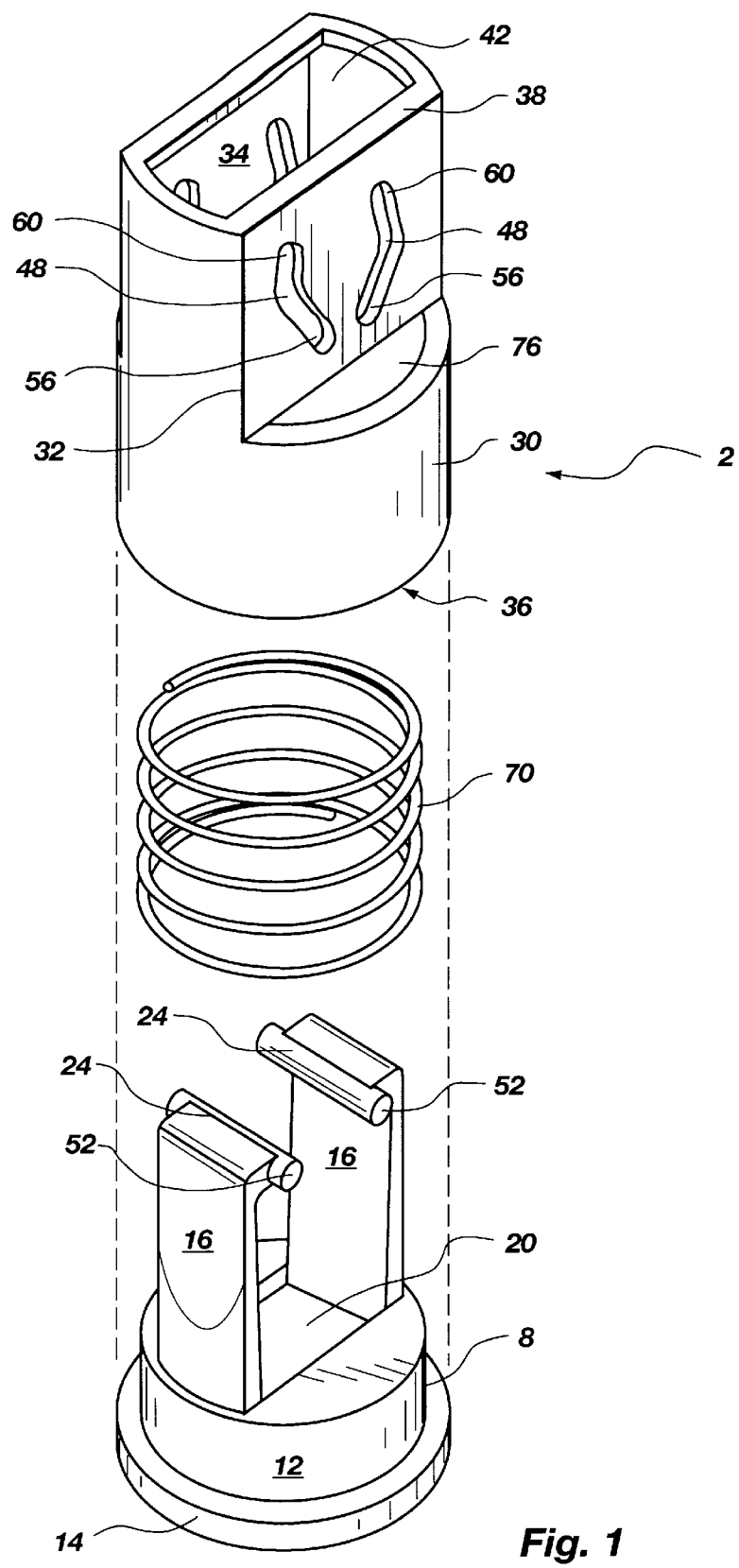
FIG. 1 shows a perspective/exploded view of the pinch clip occluder made in accordance with the principles of the present invention.

Reference will now be made to the drawings in which the various elements of the present invention; will be given numeral designations and in which the invention will be discussed so as to enable one skilled in the art to make and use the invention. Referring to FIG. 1, there is shown an exploded view of a pinch clip occluder for infusion sets, generally indicated at 2. The pinch clip 2 includes a clamp 8 having a base 12 with a flange 14 around the bottom of the base. A pair of pincher arms 16 extend from the base 12 opposite the flange 14. A passage 20 in the base 12 enables a tube of an infusion set, not shown, to pass through the base, and between the arms 16. The arms 16 are biased in a closed position so that a pair of heads 24 (one on each arm) are sufficiently close together to occlude a tube of an infusion set passing between the heads, i.e. pinching sides of the tube of the infusion set together between the heads so that solution cannot flow through that portion of the tube.

The pinch clip 2 also includes an adjustment means in the form of a housing 30 formed by a generally cylindrical wall 32. The housing 30 is designed so that the clamp 8 will fit inside a hollow 34 extending through the housing. The hollow 34 begins at an open first end 36 of the housing 30 and terminates at an open second end 38 of the housing 30 in a passage 42. When the clamp 8 is nested in the housing 30, the passage 42 in the second end 38 of the housing is in axial alignment with the passage 20 in the clamp. The axial alignment of the two passages 20 and 42 allows the tubing of an infusion set, not shown, to be passed through the pinch clip 2.

The housing 30 has a pair of channels 48 formed in at least one position along the wall 32. The channels 48 are designed to receive projections 52 extending outwardly from each head 24 on the arms 16. The channels 48 are sloped so that lower ends 56 of the channels are separated from each other by about the same distance as the heads 24 of the arms 16 when in the biased, closed position. Thus, when the projections 52 are disposed at the lower end 56 of the channels 48, the arms 16 remain in their biased state and preclude fluid from passing through an infusion set passing therethrough.

The upper ends 60 of the channels 48 are disposed further apart than the lower ends 56. Thus, if the clamp 8 is pushed upwardly into the housing 30 so that the projections 52 move from the lower ends 56 of the channels 48 to the upper ends 60, the projections 52, the heads 24 and thus the arms 16 are forced apart, overcoming the biasing of the arms. When the projections 52 are disposed at the upper end 60 of the channels 48, the heads 24 of the clamp 8 are held apart sufficiently that fluid can flow freely through the infusion set.

Also shown in FIG. 1 is a spring 70. The spring 70 is positioned adjacent the base 12 of the clamp 8 so that the bottom of the spring rests on the base. When the clamp 8 is nested in the housing 30, the top of the spring 70 rests against a lip 76 below the channels 48. The natural bias of the spring 70 is to push the clamp 8 out of the housing 30. The clamp 8, however, cannot be totally pushed out of the housing 30, because the projections 52 catch at the lower ends 56 of the channels 48. Thus, the spring 70 biases the clamp 8 into a position in which the heads 24 on the arms 16 will occlude an infusion set passing therethrough. When the clamp 8 is pushed into the housing 30, overcoming the force of the spring 70, the arms 16 will spread further apart as the projections 52 follow the channels 48 to the upper ends 60.

Figure 2:
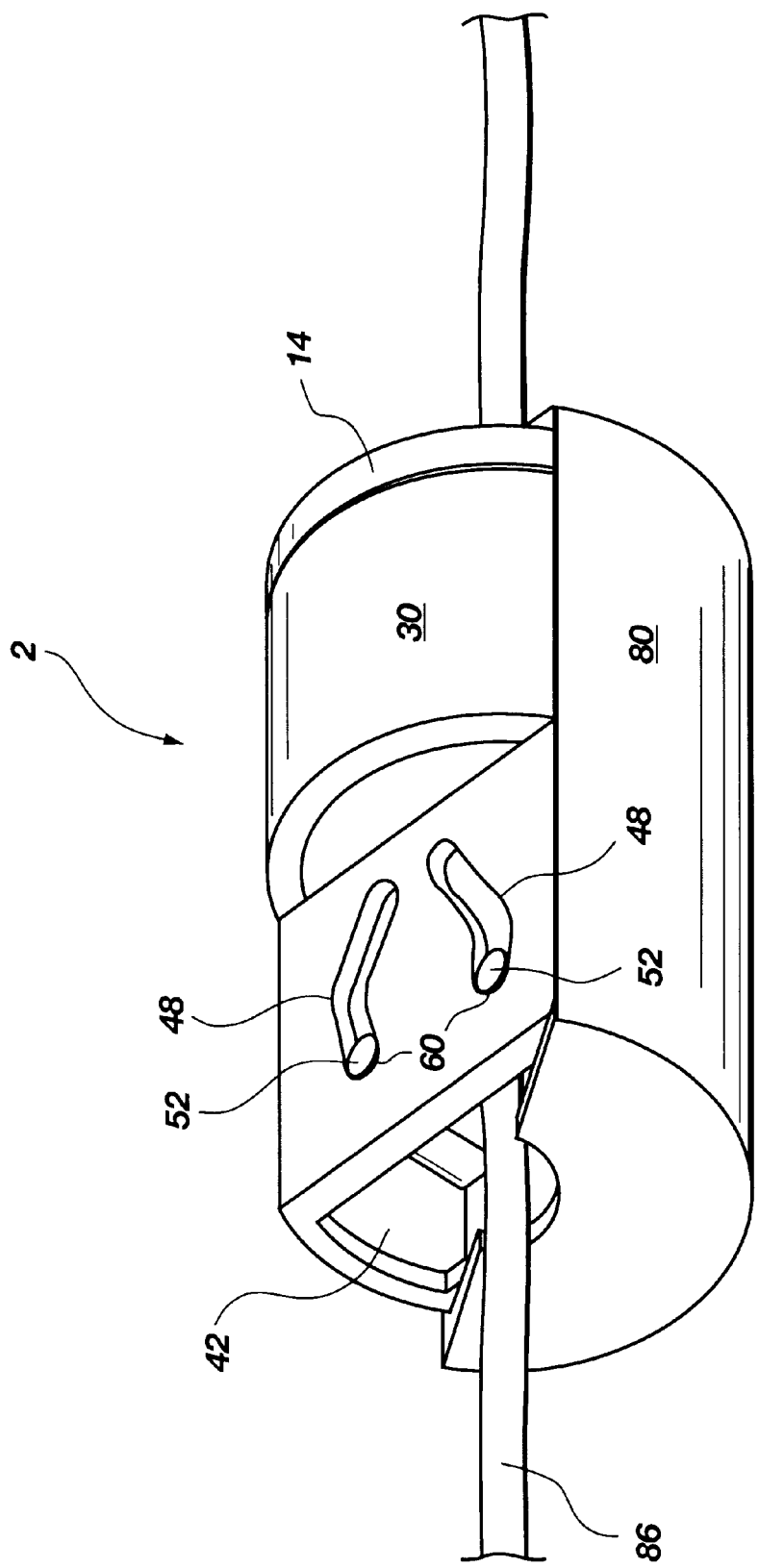
FIG. 2 shows a perspective view of the pinch clip of FIG. 1 mounted in a receptacle for maintaining the pinch clip in an open position, and a fragmented view of an infusion set passing through the pinch clip.

Referring now to FIG. 2, there is shown a perspective view of the pinch clip 2 disposed in a receptacle 80 formed as a half cylinder. In order to place the pinch clip 2 into the receptacle 80, the clamp (disposed within the housing) must be pushed into the housing 30 sufficient for the bottom of the housing to touch the flange 14, or be positioned very close thereto. When the clamp is in such a position, the projections 52 are forced to the upper ends 60 of the channels 48 so that the heads (not shown) do not occlude the infusion set 86. Such a receptacle 80 will typically be formed in devices such as enteral feeding pumps (not shown) which receive an infusion set, rather than being formed separately. No solution can flow through the infusion set 86 unless the pinch clip 2 is properly placed in the receptacle 80. Thus, medical personnel cannot accidently create a free-flow state by forgetting to thread the infusion set 86 through an enteral feeding pump, because the pinch clip 2 will occlude flow unless properly mounted in the receptacle of the feeding pump. If the infusion set is accidentally pulled out of the pump, the pinch clip 2 will automatically spring into an occluding position, thereby preventing free-flow of the solution.

Those skilled in the art will recognize that each component of the pinch clip 2 and the receptacle 80 could be made of numerous different materials. However, it is anticipated that the all of the structures, except the spring 70 (FIG. 1) will be made of polyvinylchloride (PVC), or polycarbonate materials which are inexpensive and easy to fabricate into the structures described. Such materials would also make the pinch clips 2 disposable. If greater durability is desired, materials such as advanced engineering plastics or metal can also be used. Referring now to FIG. 3A, there is shown a cross-sectional view of the pinch clip 2 in an occluding (closed) mode in that the heads 24 of the arms 16 are in a first position in the lower ends 56 of the channels 48 in the housing 30. The heads 24 are close enough together so that they pinch the sidewall of the tubing 86 together and prevent fluid flow therethrough. The clamp 8 is held in this position by the spring 70 which is fully extended.

Also shown in FIG. 3A is an infusion set connector 90 which has a first connector 94 for fitting within the tubing 86, and a second connector 98 to fit around the tubing 102. The infusion set connector 90 nests within the base 12 of the clamp 8.

Typically, an infusion set, such as that used with enteral feeding pumps, will have a pair of long sections of tubing formed from a material such as PVC, and an interspaced section of tubing made of silicone. In the present discussion, the tubing 86 represents the silicone tubing and the tubing 102 typically represents the proximal PVC tubing positioned upstream from an enteral feeding pump. The silicone tubing 86 is used to pass through an enteral feeding pump because it withstands the flexing and pulling of the pump rotor better than does the PVC tubing 102. An infusion set connector, such as connector 90, is used to connect the silicone tubing 86 to each segment of PVC tubing 102.

Referring now to FIG. 3B there is shown a side cross-sectional view of the pinch clip 2 in which the clamp 8 is forced into the housing 30. As the clamp 8 moves into the housing 30, the heads 24 of the arms 16 are forced apart by the channels 48, so that the arms are held in a second, open position. This leaves the silicone tube 86 unrestricted by the heads 24, thereby allowing solution to flow freely through the tube.

When the clamp 8 is held in the housing 30, the spring 70 is compressed as is shown in FIG. 3B. However, to maintain the position shown in FIG. 3B, the pinch clip 2 would be placed into a receptacle as shown in FIG. 2, or some other force must be applied to keep the clamp 8 positioned so that the housing 30 is adjacent the flange 14 of the base 12. Thus, if the pinch clip 2 accidently comes out of the receptacle, the spring 70 will force the clamp 8 away from the housing 30 and into the position shown in FIG. 3A. The silicone tube 86 will thereby be occluded, and a free-flow situation cannot develop.

Figure 4:
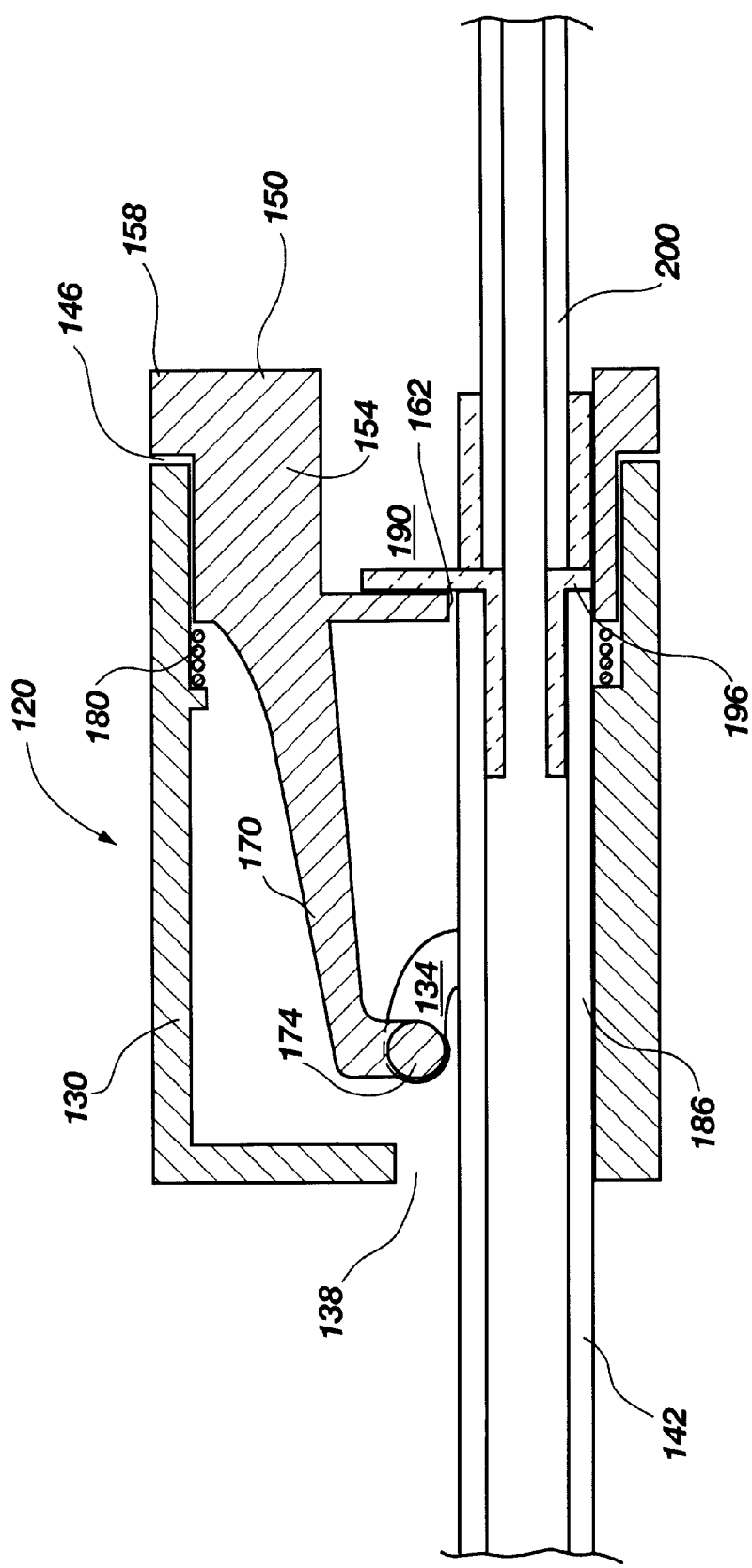
FIG. 4 shows a cross-sectional view of another embodiment of the present invention.

As was discussed regarding FIG. 3A, the connector 90 nests in the base 12 of the clamp 8 and connects the silicone tube 86 with the PVC tube 102. While this is a convenient place to make the transition between the silicone tube 86 and the PVC tube 102, the change could be made at any other place along the infusion set. Referring now to FIG. 4, there is shown an alternate embodiment of the present invention. The pinch clip 120 includes a housing 130 with a single channel 134 formed therein. As with the embodiment shown in FIGS. 1–3B, the housing 130 has an open first end 138 for containing a silicone tube 142. The opposing second end 146 is likewise open for receiving the clamp 150. The clamp 150 has a base 154 with a flange 158 and a passage 162 therethrough, similar to the embodiment discussed with respect to FIGS. 1–3B. However, instead of a pair of arms (such as those indicated at 16 in FIGS. 1, 3A and 3B) the embodiment shown in FIG. 4 has a single resilient arm 170 which extends from the base 154. A head 174 of the arm 170 is moveable between a first, closed position in which the head occludes flow through the tube 142 and a second, open position (shown in FIG. 4) in which the head is moved away from the tube so as to allow flow therethrough. A spring 180 is provided to move the base 150 away from the housing 120 and to force the head 174 into the first, closed position.

When force is applied to the clamp 150 so as to move the clamp into the housing 130, the head 174 is pushed away from the tube so as to allow fluid flow therethrough. Thus, the embodiment disclosed in FIG. 4 prevents solution flow through the tube 142 by pinching the tube between the arm 170 and a sidewall 186 the side of the housing 130, as opposed to a pair of arms as discussed above.

As with the previous embodiment, the base 154 of the clamp 150 will typically have a hollow 190 for receiving an connector 196. The connector 196 enables the silicone tube 142 to be connected to a PVC tube 200.

Each of the components shown in FIG. 4, with the exception of the spring 180, the silicone tube 142 and the PVC tube 200 will typically be made of a thermo-setting plastic material which is semi-resilient. Such materials are inexpensive and inherently disposable.

Figure 5:
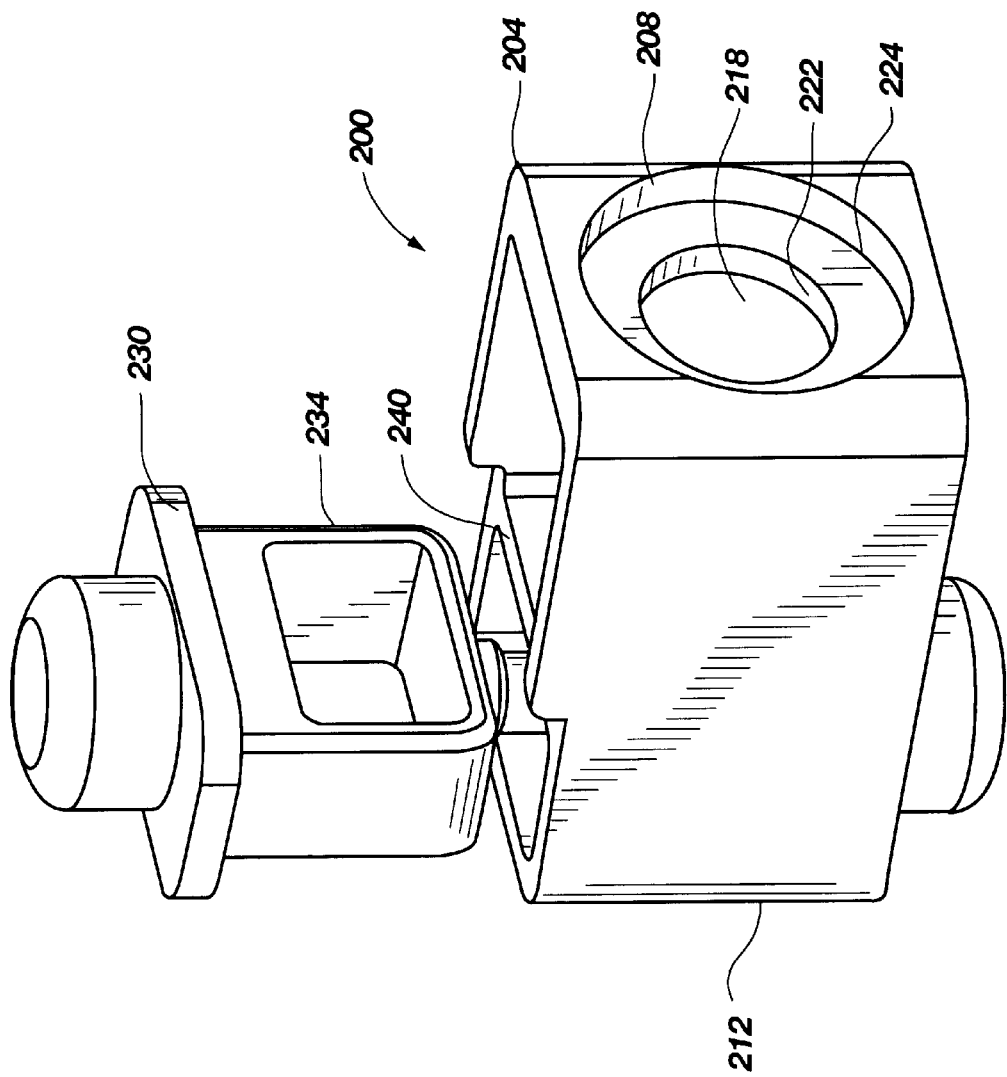
FIG. 5 shows a perspective view of yet another embodiment of the present invention.

Referring now to FIG. 5, there is shown another embodiment of the present invention. The pinch clip occluder, generally indicated at 200, includes a housing 204 having a first end 208 and a second end 212. A passage 218 extends along a long axis of the housing 204 from an opening 222 in the first end 208 to an opening (not shown) in the second end so as to enable the placement of a tube from a delivery set within the passage 218. The opening 222 may have a receiving ring 224 positioned thereabout for receiving a connector or some other component of an infusion set.

The pinch clip occluder 200 further includes a plunger 230 disposed so as to intersect the passage 218. Preferably, a long axis of the plunger 230 will be perpendicular to the long axis of the housing 204 and the passage 218. The plunger 230 includes a plunger passage 234 disposed therein. When the plunger passage 234 and the housing passage 218 are in alignment, fluid flow is allowed through a delivery set (not shown) extending through the housing 204. When the plunger passage 234 and the housing passage 218 are not in alignment, as shown in exaggeration in FIG. 5, flow through the delivery set is prevented as the tubing of the delivery set becomes pinched between the plunger 230 and an inner wall 240 of the housing 204 and a wall defining the opening (not shown) at the second end 212.

Figure 5A:
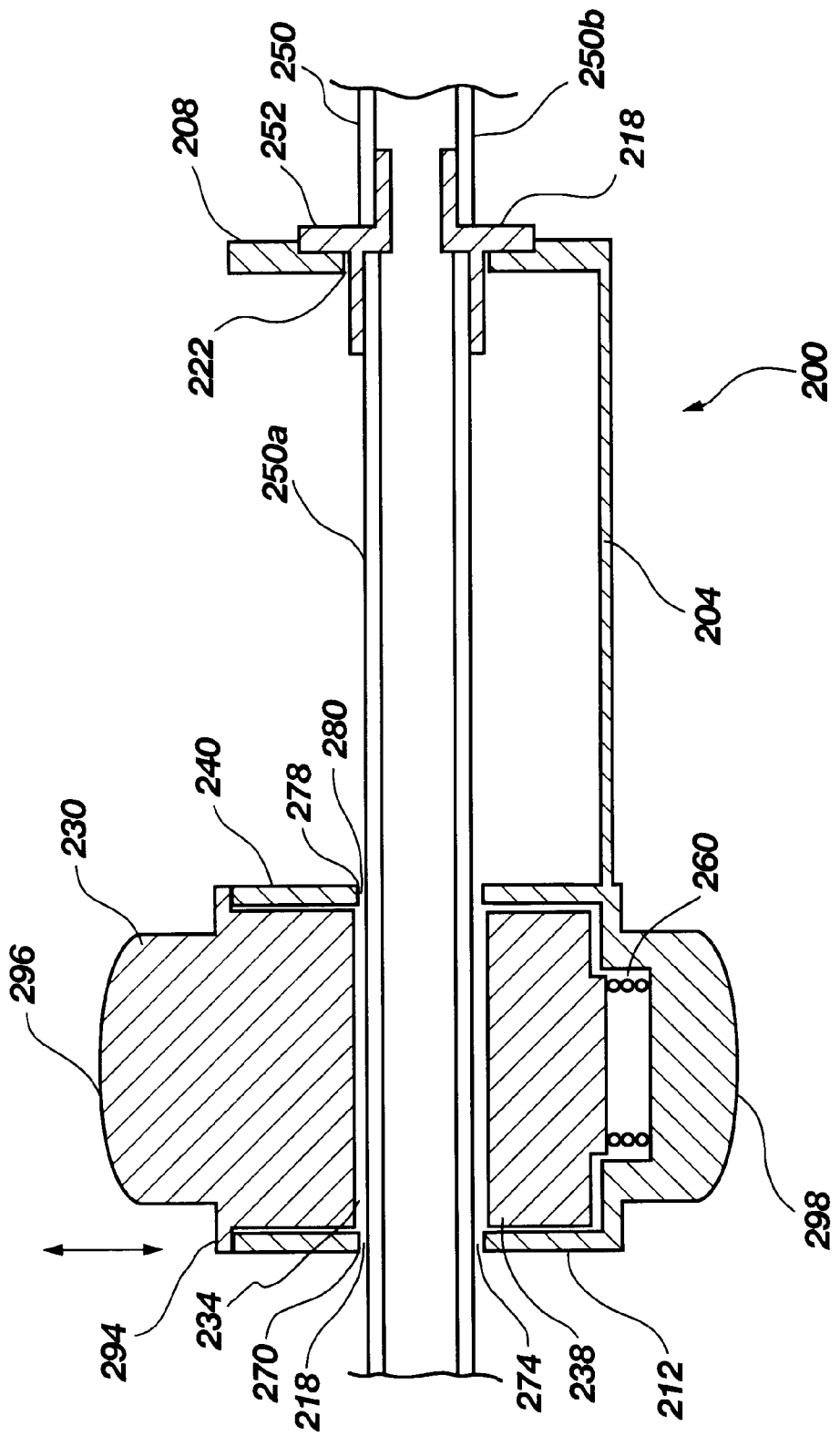
FIG. 5A shows a side cross-sectional view of the embodiment shown in FIG. 5.

Referring now to FIG. 5A, there is shown a cross-sectional view of the pinch clip occluder 200 discussed regarding FIG. 5, as well as a fragmented tube 250 of a delivery set. The tube 250 is positioned in the passage 218 to extend along the passage 218. The plunger 230 is positioned in the housing 204 adjacent the second end 212 so that the plunger passage 234 is in alignment with the housing passage 218. Thus, flow through the tube 250 of the delivery set is not occluded.

As shown in FIG. 5A, the tube 250 has a silicone section 250*a* and a section 250*b* made of polyvinylchloride (PVC) or some other suitable material. A connector 252 nests in the opening 222 and connects the two sections 250*a* and 250*b* together. Those familiar with delivery sets for use with enteral feeding pumps and the like will be familiar with such tubes.

For the plunger 230 to be in such a position in normal usage, some external force would need to force the plunger downwardly, as a spring 260 biases the plunger passage 234 into a position not in alignment with the housing passage 218. Thus, when no external pressure is applied to the plunger 230, the spring 260 forces a bottom wall 238 defining the plunger passage 234 upward so as to pinch closed the tube against an upper wall 270 defining an orifice or opening 274 in the second end 212, and an upper wall 278 defining an orifice or opening 280 in the inner wall 240. The tubing 250 through the plunger passage 234 prevents the spring 260 from displacing the plunger 230 out of the housing 204, and an upper stop 294 prevents the plunger passage 234 from passing beyond an alignment position with the housing passage 218. The upper knob 296 disposed above the stop 294 and the lower knob 298 are of similar dimensions so that the housing may be placed in an enteral feeding pump upside down from the position shown in FIGS. 5 and 5A, without affecting functionality.

Figure 6:
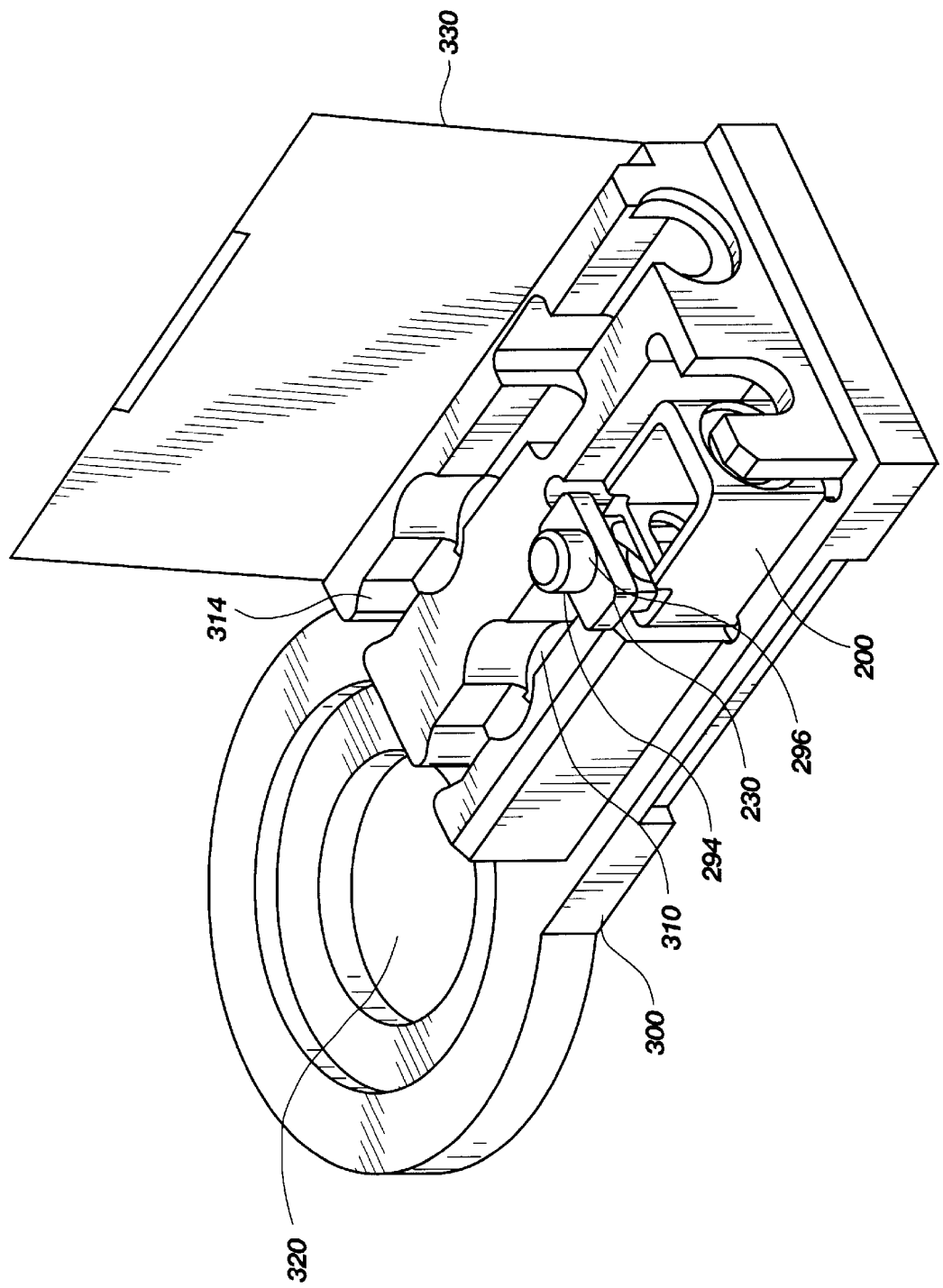
FIG. 6 shows perspective view of the embodiment of the invention discussed regarding FIGS. 5 and 5A positioned in the housing of an enteral feeding pump.

Referring now to FIG. 6, there is shown a pinch clip occluder 200 disposed in the housing 300 for an enteral feeding pump. The enteral feeding pump housing 300 includes a pair of channels 310 and 314 for holding a delivery set tube, such as tube 250 discussed in FIG. 5A. In use, the tube is placed in one channel 310, wrapped about a motor unit (not shown) which is placed in the opening 320, and then positioned in the second channel 314. If the tube is not properly wrapped about the motor unit and placed in the channels 310 and 314, a free-flow condition may develop. However, the present invention prevents such a situation from developing.

As shown in FIG. 6, the pinch clip occluder 200 is positioned along the channel 310. The plunger 230 is positioned so as to occlude flow through a tube disposed in the channel 310. To overcome the biased closed position of the plunger 230, an external force must be applied. This is typically done by closing a cover 330 which is connected to the housing 300. When closed, the cover 330 applies downward force on the plunger 230 so that the plunger passage 234 and the housing passage are in alignment. However, if the tube of the delivery set is not properly loaded in the channels 310 and 314, the cover is unable to close and the plunger 230 is not forced downwardly. Thus, the pinch clip occluder 200 prevents flow through the enteral feeding pump unless the delivery set is properly loaded. Once the cover 330 is closed, the enteral feeding pump may function normally.

Figure 7:
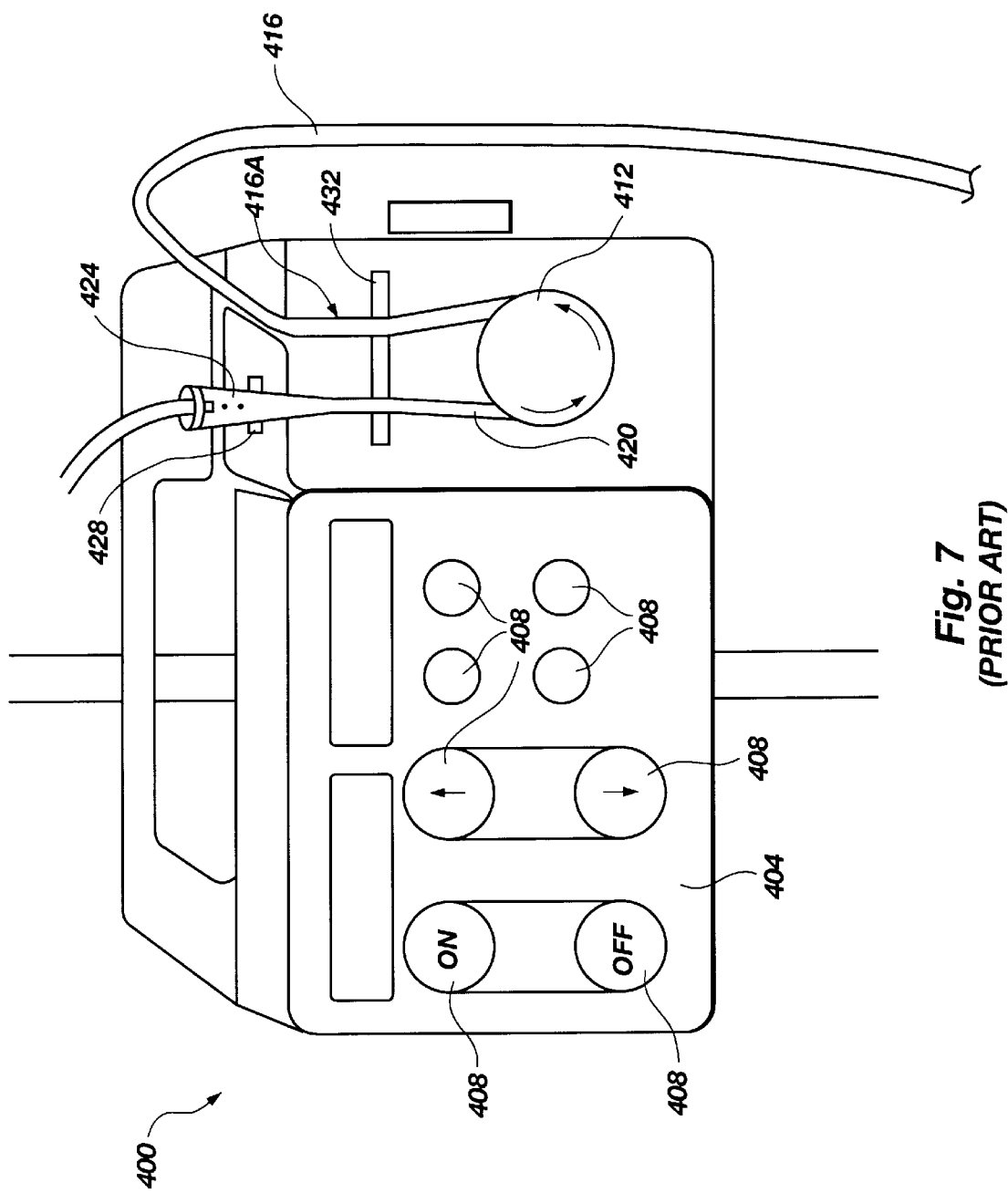
FIG. 7 shows a front view of an enteral feeding pump made in accordance with the teachings of the prior art.

Turning now to FIG. 7, there is shown a perspective view of a pump, generally indicated at 400, which is designed to control fluid flow through an infusion set and into the patient. The pump 400 includes a control panel 404 which has a plurality of buttons 408 or other devices for controlling the actuation of the pump. The pump 400 operates to deliver a predetermined dose of enteral feeding solution to a patient by rotation of a rotor 412 (shown in close-up in FIG. 7A). An infusion set 416 is mounted on the pump so that a resilient portion 420 of the infusion set wraps around the rotor 412. Each rotation or partial rotation of the rotor 412 causes a predetermined amount of enteral feeding solution to be advanced through the infusion set 416 and delivered to the patient.

In order to assure that the rotor 412 is providing the proper amount of enteral feeding solution, a drip chamber 424 is formed along the infusion set 416. An optical sensor 428 is disposed in the enteral feeding pump 400 and monitors the drip rate of the solution in the drip chamber 424. The drip rate of the solution is used to calculate an actual delivery rate of the solution. If the delivery rate of the solution is significantly greater or less than desired, the enteral feeding pump can determine that the patient is receiving an inappropriate dose of solution and sound an alarm. Unfortunately, it is common for health care workers to turn down the alarms at night and other times to reduce noise.

The drip chamber 424 and a distal portion 416*a* of the tubing of the infusion set 416 are held by a retention plate 432 which is affixed to the pump. The retention plate 432 holds the drip chamber 424 and the distal portion 416*a* to ensure the resilient portion 420 of the infusion set 416 is held against the rotor 412. Unfortunately, both the drip chamber 424 and the distal portion 416*a* of the infusion set can be pulled out of the retention plate 432. If either of these events occurs, the infusion set 416 can be left in a free-flow condition wherein the patient receives an excessive dose of the solution.

In addition to the infusion set 416 being accidentally pulled from the retention plate 432, occasionally a health care profession may forget to properly load the infusion set after opening the roller clamp (not shown) or other flow restricting device. This typically occurs when the health care professional is distracted temporarily by some urgent matter. When the infusion set 416 is not loaded properly, a free-flow condition can develop. As mentioned in the background section above, the existence of a free-flow condition can be extremely harmful to the patient. Recently a patient died when a nurse forgot to load the infusion set properly in a pump similar to that shown in FIG. 7. The excessive inflow of enteral feeding solution caused the patient to go into cardiac arrest.

Figure 7A:
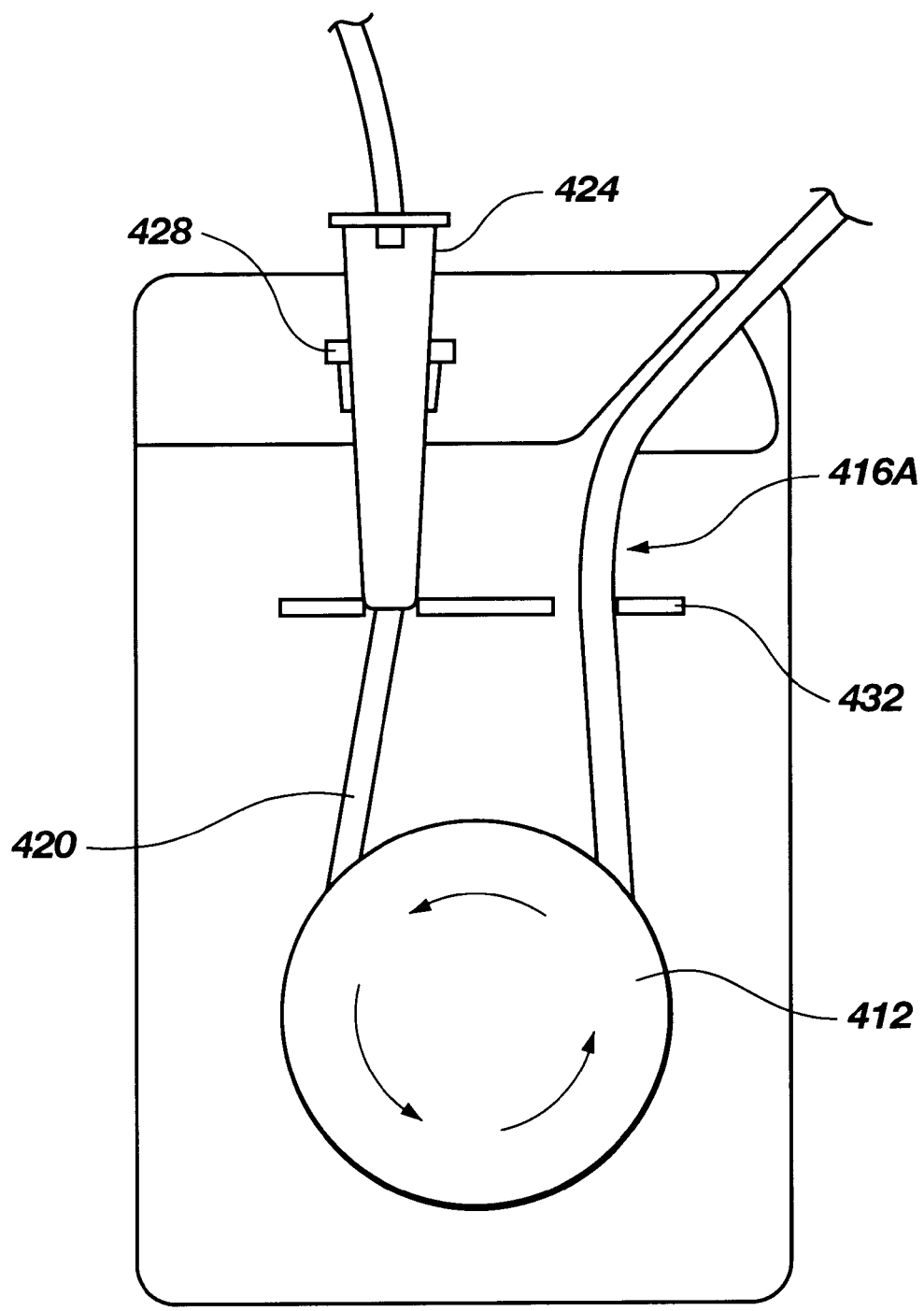
FIG. 7A shows a close-up view of an infusion set and the rotor mechanism of FIG. 7.
Figure 8A:
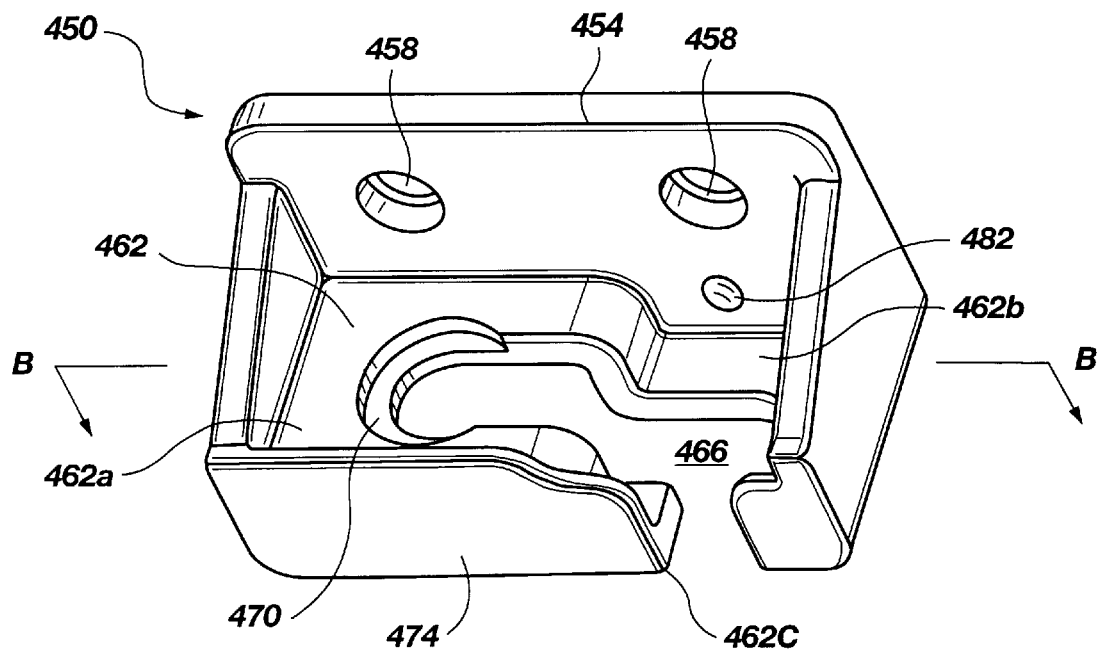
FIG. 8A shows a perspective view of an adapter configured for attachment to the enteral feeding pump of FIG. 7.

Turning now to FIG. 8A, there is shown a perspective view of an adapter configured for attachment to the enteral feeding pump of FIG. 7. The adapter, generally indicated at 450 includes a back plate 454 with a plurality of holes 458 formed therein. The holes 458 in the back plate 454 are in the same position as corresponding holes (not shown) in the retention plate 432 (FIGS. 7 and 7A) which are used to secure the retention plate 432 to the pump. Thus, the retention plate may be removed and the adapter 450 substituted in its place simply by removing a pair of screws, removing the retention plate 432, aligning the adapter 450 and reinserting the screws.

Extending forwardly from the back plate 454 is a bottom wall 462 which is contoured to provide first and second levels 462*a* and 462*b*, respectively. A channel 466 is formed in the bottom wall 462. The channel 466 extends from a forward extreme 462*c* of the bottom wall 462 opposite the back plate 454, through the second level 462*a* and into the first level 462*a*.

Figure 8D:
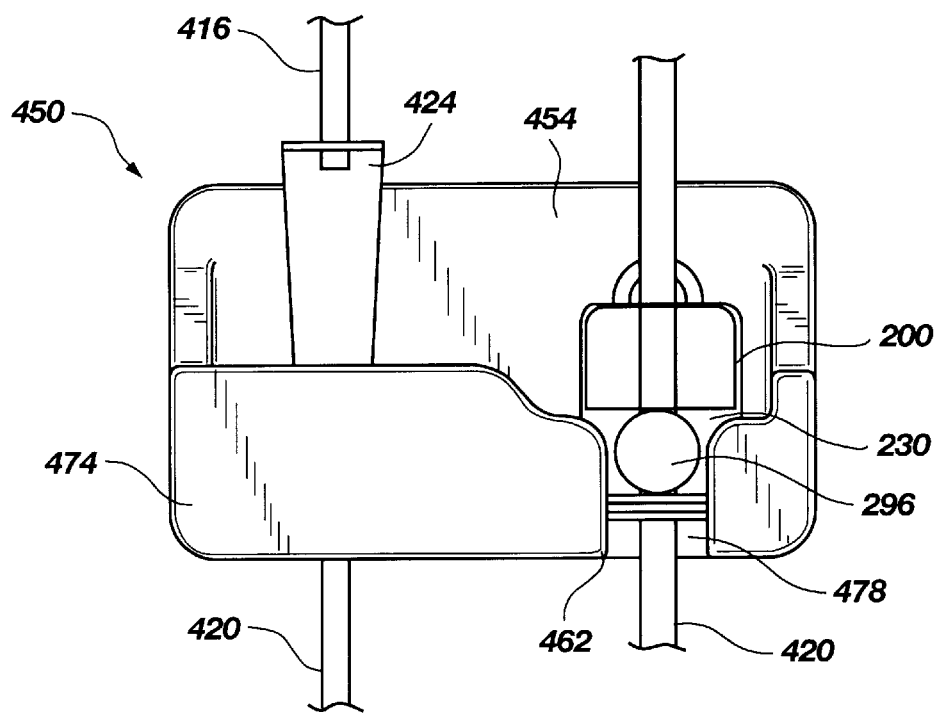
FIG. 8D shows a close-up view of a pinch clip occluder and infusion set disposed within the adapter in accordance with the principles of the present invention.

At the end of the channel 466 in the first level 462*a*, a groove 470 is formed. The groove 470 is configured to receive the bottom end of a drip chamber, such as the drip chamber 424 shown in FIGS. 7 and 7A. Unlike the retention plate 423 (FIGS. 7 and 7*a*) which allows the drip chamber 424 and connected tubing of the infusion set 416 to be slid into the retention plate linearly, the adapter 450 requires the drip chamber and associated tubing be moved in an L-shaped pattern until the drip chamber nests in the groove 470. FIG. 8D shows a front view of the drip chamber 424 disposed in the groove (not shown). Removal of the drip chamber 424 requires a similar L-shaped movement pattern.

While the drip chamber nests in the groove 470 in the first level 462*a* at a predetermined height relative to the optical sensor 428, etc., the second level 462*b* is disposed at a lower level to enable the adapter 450 to receive a pinch clip occluder, such as that shown in FIGS. 5 through 6 above and indicated at numeral 200. As will be explained in detail below, placing the pinch clip occulder in the adapter serves both to provide a free-flow prevention device along the infusion set 416 and to essentially lock the drip chamber 424 in place so that it cannot be accidentally pulled away from the pump 400, thereby causing a free-flow situation.

Preferably, the adapter 450 has a front wall 474 with a contoured opening 478 at the point of the forward extreme 462*c* of the bottom wall 462 where the channel 466 begins. The contoured opening allows the drip chamber 424 and associated tubing to be slid into place, and allows for a pinch clip occluder 200 to nest down into an abutment with the second level 462*b* of the bottom wall 462. Preferably, the opening 478 is sized similarly to the size of the knob 296 so that the interaction of the knob 296 and the opening tend to maintain the pinch clip occluder 200 in place.

In order to load the pinch clip occluder 200, the plunger 230 is depressed and the pinch clip occluder is slid vertically downward between the front wall 474 and the back plate 454. Preferably the back wall 454 also includes a detent 482 which will receive the knob 298 (FIG. 5A), or some other contour which will help ensure proper placement. While the knobs and contours are not necessary, they assist in ensuring that the pinch clip occluder 200 is properly position in the adapter 450.

The use of the adapter and the pinch clip occluder 200 helps to prevent free-flow situations in several ways. First, placement of the pinch clip occluder 200 in the adapter 450 locks the drip chamber 424 and associated tubing in place. Thus, the drip chamber 424 cannot be removed from the adapter 450 so as to disassociate the tubing 420 and the rotor 412 (FIGS. 7 and 7A). Second, the very use of the pinch clip occluder 200 on the infusion set 416 helps to prevent free-flow conditions, as the pinch clip will not allow fluid flow until the plunger 230 is depressed. Third, biasing of the plunger 230 by the internal spring 260 causes the plunger to forcefully engage the front wall 474 or back plate 454 of the adapter 450. This forceful engagement helps prevent accidental removal of the pinch clip occluder and the remainder of the infusion set from the adapter 450 and from engagement with the rotor 412. Thus, when using the adapter 450 and a pinch clip occluder 200, it is highly unlikely that a free-flow condition will develop.

Figure 8B:
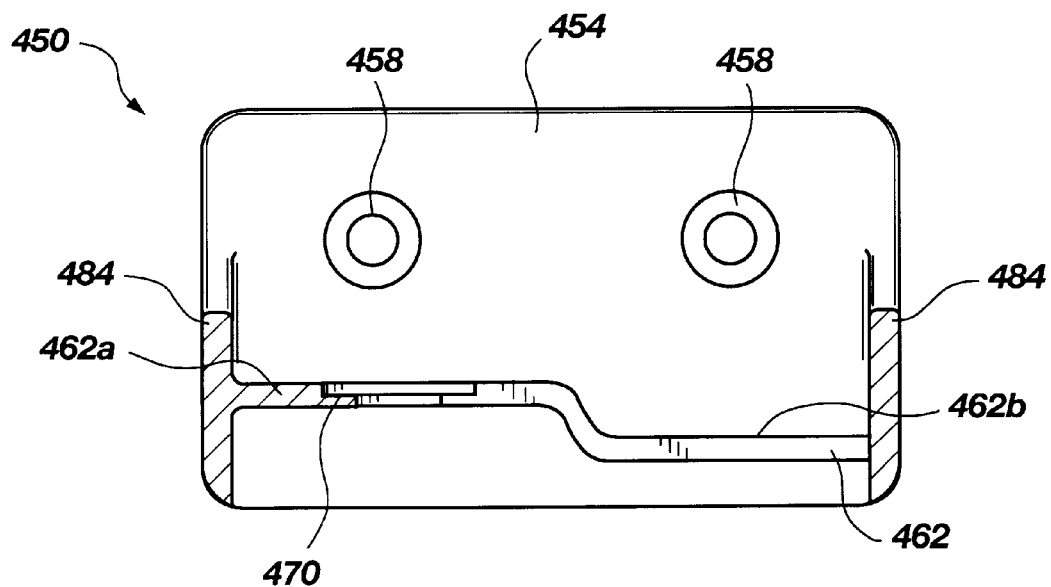
FIG. 8B shows a cross-sectional view of the adapter taken along the line B—B in FIG. 8A.

Turning now to FIG. 8B, there is shown a cross-sectional view of the adapter 450 taken along the line B—B in FIG. 8A. The cross-sectional view shows the rear plate 454 with the holes 458 formed therein for attaching the adapter 450 to the enteral feeding pump 400. Extending forwardly of the back plate 454 is the bottom wall 462 and a pair of side walls 484.

As was mentioned previously, the bottom wall 462 is preferably contoured so as to provide a first, upper level 462a and a second, lower level 462b. The first, upper level 462a is positioned so that when a drip chamber 424 (FIGS. 7, 7A and 8D) is placed thereon, the drip chamber is in the proper position for monitoring by the optical sensor 428 (FIGS. 7 and 7A).

In contrast, the second, lower level 462b is positioned lower to allow for adequate nesting of the pinch clip occluder 200 as shown in FIG. 8D. While the contoured configuration of the bottom wall 462 shown in FIG. 8B is believed to be the preferred embodiment when using the pump 400 shown in FIG. 7 and the pinch clip occluder 200 shown in FIGS. 5 through 6, it is important to appreciate that other configurations could be used with this combination of pump and pinch clip occluder. Additionally, different combinations of pump configurations and pinch clip configurations could have different preferred embodiments. For example, if the pinch clip shown in FIG. 1 were to be used, the presence of a front wall 474 would be relatively unimportant adjacent the pinch clip. However, an upper wall would be necessary to hold the pinch clip in the open configuration.

Figure 8C:
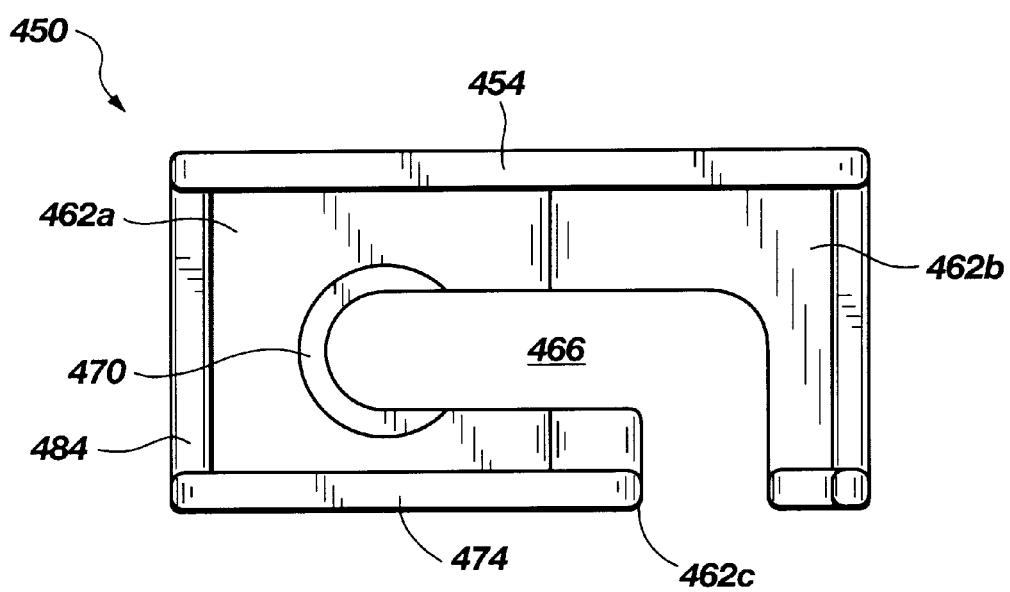
FIG. 8C shows a top view of the adapter shown in FIGS. 8A and 8B.

Turning now to FIG. 8C, there is shown a top view of the adapter 450. The top view is provided to emphasize the 1-shaped channel 466 which extends from the front wall 474, through the second, lower level 462b of the bottom wall 462, and into the first, upper level 462a. Also shown in FIG. 8C is the groove 470 which is formed at the end of the channel 466 to receive the base of the drip chamber 424 (FIGS. 7, 7A and 8D). While placement of the drip chamber 424 in the adapter 450 takes slightly more agility than is required to load the drip chamber in the retention plate 432 shown in FIGS. 7 and 7A, it provides a significant improvement in preventing the drip chamber from accidentally being moved and thereby disassociating the infusion set 416 (FIGS. 7, 7A and 8B) from the rotor 412 (FIGS. 7 and 7A).

The adapter 450 shown in FIGS. 8A through 8D is a significant improvement over the retention plates 432 of the prior art. It is inexpensive to manufacture and provides a significant decrease in the risk of developing free-flow situations. While the embodiment shown in FIG. 8A is currently believed to be the preferred embodiment, numerous other embodiments may be developed which are equally advantageous. In the manner described, a pinch clip occluder system is provided. In one embodiment, a pinch clip occluder utilizes a clamping mechanism with at least one arm nested at least partially within a housing which serves as an adjustment mechanism by moving the arm between a position in which the arm occludes flow through and infusion set, and a position in which it allows free-flow through the infusion set. In another embodiment, a moveable plunger which has a plunger passage alignable with a housing passage occludes flow through the housing unless an external pressure is applied. In accordance with still further aspects of the invention, adapters may be provided for retrofit on existing pumps or as original equipment on new pumps which allow a pinch clip occluder to be used with enteral feeding pumps and other pumps which utilize infusion sets.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. An adapter for selectively holding an infusion set having a first portion and a second portion with a resilient portion between the first portion and second portion in communication with a pump mechanism the adapter comprising:

means for attaching the adapter to a pump mechanism;

a wall extending from the means for attacking, the wall defining an infusion set receiving channel configured in an L-shape with an opening at one end and a opposing end which is closed for receiving first and second portions of an infusion set such that a resilient portion between the first and second portions of the infusion set extends outside the channel and for preventing removal of the first portion of the infusion set through the opening while the second portion of the infusion set is disposed therein, and wherein the closed end has a groove formed therein for receiving a drip chamber.

2. The adapter according to claim 1, wherein the wall extending from the adapter is contoured to form a first, upper level, and a second lower level disposed lower than the first upper level, and wherein the channel extends at least through a part of the first, upper level and a part of the second, lower level.

3. The adapter according to claim 2, end, and wherein the open end is formed in the second, lower level and wherein the closed end is formed in the first, upper level.

4. The adapter according to claim 1, wherein the wall extending from the means for attaching is disposed generally horizontally, and further comprising generally vertical wall means extending upwardly from the wall extending from the means for attaching so as to define a containment area between the means for attaching, the wall extending from the means for attaching; and the generally vertical wall means so as to define a containment area configured for receiving a pinch clip occluder.

5. The adapter according to claim 4, wherein the means for attaching comprises a back plate having a plurality of holes formed therein, and wherein a detent is formed in the back plate for receiving a portion of a pinch clip occluder.

6. The adapter according to claim 1, wherein the adapter further comprises means for holding a pinch clip occluder adjacent the wall extending from the means for attaching.

7. An adapter system for preventing free-flow, the adapter system comprising:

an infusion set having an elongate tube, a drip chamber disposed along the tube, and a pinch clip disposed on the tube so as to selectively prevent fluid flow along the tube; and an adapter configured for attachment to pump mechanism, the adapter having a lower wall with a channel formed therein for receiving first and second sections of the elongate tube, the adapter further comprising wall means for holding the pinch clip in an open configuration wherein the pinch clip does not prevent fluid flow through the elongate tube.

8. An adapter system according to claim 7, wherein the lower wall is contoured to have a first upper level and a second lower level with an upper surface disposed below the first upper level.

9. An adapter system according to claim 8, wherein the channel is formed with an opening in the second, lower level and an ending in the first, upper level.

10. An adapter system according to claim 9, wherein the channel is L-shaped.

11. An adapter system according to claim 7, wherein the adapter comprises a back plate configured for attachment to a pump mechanism, the back plate being disposed generally perpendicularly from the lower wall, and an outer wall disposed generally parallel to the back plate on an opposite side of the lower wall.

12. An adapter system according to claim 11, wherein the back plate and the outer wall are configured to receive the pinch clip of the infusion set and to maintain the pinch clip in an open position wherein fluid flow through the elongate tube is permitted.

13. An adapter system according to claim 12, wherein the outer wall has an opening configured for nestingly receiving a portion of the pinch clip.

14. An adapter system according to claim 12, wherein the back plate has a detent formed therein for receiving a portion of the pinch clip.

15. An adapter system according to claim 7, wherein the lower wall is configured for receiving the drip chamber disposed along the elongate tube of the infusion set.

16. An adapter system according to claim 15, of the channel has a groove configured for receiving a drip chamber.

17. An adapter system according to claim 7, wherein the channel is L-shaped.

18. A method for loading an infusion set on a pump mechanism so as to prevent free-flow conditions, the method comprising:

(a) selecting a pump mechanism having an adapter disposed thereon with a channel for receiving first and second sections of an infusion set;

(b) inserting a first section of an infusion set into the channel;

(c) inserting a second section of the infusion set having a pinch clip disposed thereon into the channel of the adapter and anchoring the pinch clip therein to allow fluid flow through the infusion set when the pinch clip is disposed in the adapter, and such that fluid flow through the infusion set is prevented when the pinch clip is pulled from the adapter.

19. The method according to claim 18, wherein L-shaped channel is.

20. The method according to claim 19, wherein and wherein the method further comprises selecting an infusion set having a drip chamber disposed along a first section of the infusion set.

21. The method according to claim 18, wherein the adapter has a lower wall which is contoured to form a first, upper level and a second lower level positioned lower than the first upper level.

22. The method according to claim 21, wherein the channel formed in the adapter extends from an opening in the second, lower level to an ending in the first, upper level.

23. An adapter for selectively holding an infusion set in communication with a pump mechanism, the adapter comprising:

means for attaching the adapter to a pump mechanism a wall extending from the means for attaching, the wall having an infusion set receiving channel formed through the wall, the infusion set receiving channel having an open end and a closed end, and being configured for receiving a first portion of the infusion set at the closed end and a second portion of the infusion set adjacent the open end, the channel being further configured such that the first portion of the infusion set cannot be slid out through the open end while the second portion of the infusion set is disposed in the channel, wherein the wall is generally horizontal, and wherein the infusion set receiving channel extends generally from the open end to the closed end.

24. The adapter of claim 23, wherein the closed end has a groove formed therein for receiving a drip chamber.

25. An adapter for selectively holding an infusion set in communication with a pump mechanism, the adapter comprising:

a back plate configured for attachment to a pump mechanism;

a wall extending from the back plate, the wall having a channel formed therethrough for receiving a first portion and a second portion of an infusion set, the wall comprising a groove formed along the channel for receiving a drip chamber formed along the first portion of the infusion set; and a front wall attached to the wall opposite the back plate, and wherein the back plate, the wall and the front wall are configured for nestingly receiving a pinch clip occluder and for holding the pinch clip occluder in an open, fluid flow accommodating position.

26. The adapter of claim 25, wherein the front wall has an opening formed therein for receiving and maintaining a portion of a pinch clip occluder disposed along the second portion of the infusion set while the second portion of the infusion set is disposed within the channel.

* * * * *

UNITED STATES PATENT AND TRADEMARK OFFICE
CERTIFICATE OF CORRECTION

| | | |
|---|---|---|
| PATENT NO. | : 6,142,979 | |
| APPLICATION NO. | : 09/158590 | |
| DATED | : November 7, 2000 | |
| INVENTOR(S) | : McNally et al. | |

It is certified that error appears in the above-identified patent and that said Letters Patent is hereby corrected as shown below:

Title Page
Item [75] reads "Inventors: David J. McNally, Bluffdale; Al Halbert, Salt Lake City, both of Utah" should read --Inventors: David J. McNally, Salt Lake City; Al Halbert, Bluffdale, both of Utah--

Title Page Item [63], Related U.S. Application Data and Col. 1, lines 9-10, reads "..., which is a continuation of application No. 08/410,912, Mar. 21, 1998, abandoned." should read --..., which is a continuation of application No. 08/410,912, Mar. 27, 1995, abandoned.--

Title Page Item [57], ABSTRACT, lines 4-5 reads "... when the pinch clip occluder is properly position, ..." should read --... when the pinch clip occluder is properly positioned, ...--

Column 10:
Line 39 reads "a wall extending from the means for attacking, the wall"
should read --a wall extending from the means for attaching, the wall--

Line 41 reads "... and a opposing"
should read --... and an opposing--

Line 45 reads "extends outside the channel and for preventing removal"
should read --extends outside the channel, and for preventing removal--

Line 56 reads "..., end, and wherein the"
should read --..., wherein the--

Column 11
Line 14 reads "... to pump mechanism" should read --... to a pump mechanism--
Line 51 reads "..., of the"
should read --..., wherein an end of the--

UNITED STATES PATENT AND TRADEMARK OFFICE
CERTIFICATE OF CORRECTION

PATENT NO. : 6,142,979
APPLICATION NO. : 09/158590
DATED : November 7, 2000
INVENTOR(S) : McNally et al.

It is certified that error appears in the above-identified patent and that said Letters Patent is hereby corrected as shown below:

Column 12
Line 8 & 9 read "..., wherein L-shaped channel is."
    should read --..., wherein the channel is L-shaped.--

Line 10 reads "..., wherein and"
    should read --,--

Line 11 & 12 read "wherein the method further comprises selecting an infusion set having ..." should read --wherein the adapter has a groove disposed about the channel for receiving ...--

Line 36 reads "generally from the open end to the closed end."
    should read --generally horizontally from the open end to the closed end.--

Signed and Sealed this

Fourth Day of September, 2007

JON W. DUDAS
*Director of the United States Patent and Trademark Office*